US012691003B2

(12) United States Patent
Long

(10) Patent No.: US 12,691,003 B2
(45) Date of Patent: Jul. 28, 2026

(54) INTELLIGENT SHARED CRYOGENIC PHYSICAL THERAPY SYSTEM

(71) Applicant: Zhigang Long, Beijing (CN)

(72) Inventor: Zhigang Long, Beijing (CN)

( * ) Notice: Subject to any disclaimer, the term of this patent is extended or adjusted under 35 U.S.C. 154(b) by 448 days.

(21) Appl. No.: 18/233,505

(22) Filed: Aug. 14, 2023

(65) Prior Publication Data

US 2024/0050270 A1      Feb. 15, 2024

(30) Foreign Application Priority Data

Aug. 15, 2022    (CN) .......................... 202210974216.2

(51) Int. Cl.
*A61F 7/00*          (2006.01)
(52) U.S. Cl.
CPC .... *A61F 7/0053* (2013.01); *A61F 2007/0093* (2013.01)
(58) Field of Classification Search
CPC ........... A61F 7/0053; A61F 2007/0093; G06Q 10/02; G06Q 10/063; G06Q 10/10;
(Continued)

(56) References Cited

U.S. PATENT DOCUMENTS 11,123,220 B1 *  9/2021 Mann, III ............... A61B 18/02
2003/0023460 A1    1/2003 Ackermann et al.
(Continued)

FOREIGN PATENT DOCUMENTS

CN         107710273 A      2/2018
CN         109147885 A      1/2019
(Continued)

OTHER PUBLICATIONS

Wang X, Ren Y, Liu J. Liquid Metal Enabled Electrobiology: A New Frontier to Tackle Disease Challenges. Micromachines (Basel). Jul. 21, 2018;9(7):360. doi: 10.3390/mi9070360. PMID: 30424293; PMCID: PMC6082282. (Year: 2018).*

(Continued)

*Primary Examiner* — Sun M Li
(74) *Attorney, Agent, or Firm* — Bret E. Field; Bozicevic, Field & Francis LLP

(57)          ABSTRACT

The embodiments of the invention provide an intelligent shared cryogenic physical therapy system, including cryogenic physical therapy devices, human-machine interaction devices and a server. The server is configured to acquire target location information and recommend a cryogenic physical therapy device based on a relationship between the target location information and pre-recorded location information of each of the cryogenic physical therapy devices; and send a use request to a human-machine interaction device when a target cryogenic physical therapy device is selected and it is determined that the account balance meets a fee deduction condition. The human-machine interaction device can acquire the use request and generate the control instruction. A programmable controller of the cryogenic physical therapy device is configured to control the physical therapy module to perform an operation indicated by the control instruction when receiving the control instruction. After finishing the cryogenic physical therapy, the human-machine interaction device is configured to send a fee deduction request to the server, so that the server can update the account balance when receiving the fee deduction request. The user does not need to go to a specific service merchant, and can select a suitable cryogenic physical therapy device according to actual conditions.

7 Claims, 7 Drawing Sheets

(58) Field of Classification Search
CPC .... G06Q 20/14; G06Q 20/145; G06Q 20/401;
G06Q 20/4037; G06Q 30/0283; G06Q
30/0609; G06Q 30/0631; G06Q 30/0639;
G06Q 50/22; G16H 20/30; G16H 40/67;
G07F 17/0042; G07F 17/0021; H04L
67/12
See application file for complete search history.

(56) References Cited

U.S. PATENT DOCUMENTS

| 2005/0004635 | A1* | 1/2005 | Brojek | A61F 7/0053 |
| | | | | 607/104 |
| 2009/0276272 | A1* | 11/2009 | Hughes | G07F 17/0014 |
| | | | | 235/382 |
| 2012/0259650 | A1* | 10/2012 | Mallon | G16H 40/67 |
| | | | | 705/2 |
| 2013/0025302 | A1* | 1/2013 | Lyubchenko | A61F 7/0053 |
| | | | | 62/89 |
| 2016/0089262 | A1* | 3/2016 | Kuehne | A61F 7/0053 |
| | | | | 606/20 |
| 2019/0065681 | A1 | 2/2019 | Gmeiner | |
| 2022/0062031 | A1* | 3/2022 | Geurtin | A61H 33/6068 |
| 2022/0181017 | A1* | 6/2022 | Nakashima | G06Q 50/40 |

FOREIGN PATENT DOCUMENTS

| CN | 109636380 | A | | 4/2019 | |
| CN | 114886654 | A | * | 8/2022 | A61M 11/00 |
| JP | 2016512070 | A | | 4/2016 | |
| WO | WO-2018106133 | A1 | * | 6/2018 | A61F 7/0053 |
| WO | WO-2021088967 | A1 | * | 5/2021 | A61F 7/0085 |
| WO | WO2022015268 | A2 | | 1/2022 | |

OTHER PUBLICATIONS

Wang X, Ren Y, Liu J. Liquid Metal Enabled Electrobiology: A New Frontier to Tackle Disease Challenges. Micromachines (Basel). Jul. 21, 2018;9(7):360. doi: 10.3390/mi9070360. PMID: 30424293; PMCID: PMC6082282.V (Year: 2018).*
Straburzyńska-Lupa A, Kasprzak MP, Romanowski MW, Kwaśniewska A, Romanowski W, Iskra M, Rutkowski R. The Effect of Whole-Body Cryotherapy at Different Temperatures on Proinflammatory Cytokines, Oxidative Stress Parameters, and Disease Activity in Patients with Ankylosing Spondylitis. Oxid Med Cell Long (Year: 2018).*
Health Club Management 259, Jul. 1, 2018, Retrieved from the Internet: URL:https://www.healthclubmanagement.co.uk/pdf/HCM_Jul_2018.pdf on Dec. 7, 2023, 100 pages.

* cited by examiner

INTELLIGENT SHARED CRYOGENIC PHYSICAL THERAPY SYSTEM

TECHNICAL FIELD

The invention relates to the technical field of cryogenic physical therapy, in particular to an intelligent shared cryogenic physical therapy system.

BACKGROUND

With the acceleration of modern life rhythm, more and more people are in sub-health state, and it is extremely unfavorable to human health to be in sub-health state for a long time. As an emerging physiotherapy technology, cryogenic physical therapy technology is gradually getting into the field of vision of the masses from the traditional medical field. The cryogenic physical therapy is the process of exposing the human body to an extremely low temperature (usually below −110° C.) environment for a period of time, such as about 2-3 minutes, and stimulate the skin of a user through low temperature, so that endorphin is released in the body of the user, and the functional effects of accelerating blood circulation, continuously burning fat, increasing skin elasticity, and eliminating muscle fatigue and the like are achieved.

Due to the high selling price and maintenance cost of a cryogenic physical therapy device, a service merchant of the cryogenic physical therapy device usually installs the cryogenic physical therapy device in a certain fixed area to reduce operational service costs. When a user wants to perform cryogenic physical therapy, the user first needs to go to the area and recharge or apply for member services at the service merchant before starting to perform cryogenic physical therapy.

Due to the high selling price and maintenance cost of a cryogenic physical therapy device, a service merchant of the cryogenic physical therapy device usually installs the cryogenic physical therapy device in a certain fixed area to reduce operational service costs. When a user wants to perform cryogenic physical therapy, the user first needs to go to the area and recharge or apply for member services at the service merchant before starting to perform cryogenic physical therapy.

SUMMARY

An object of embodiments of the invention is to provide an intelligent shared cryogenic physical therapy system, so as to allow a user to select a suitable cryogenic physical therapy device according to actual conditions to perform cryogenic physical therapy quickly. The specific technical solution is as follows.

An embodiment of the invention provides an intelligent shared cryogenic physical therapy system, including cryogenic physical therapy devices, human-machine interaction devices and a server, wherein each of the cryogenic physical therapy devices includes a physical therapy module and a programmable controller; each of the human-machine interaction devices includes a processing unit and a network module; wherein:

the programmable controller is electrically connected with the physical therapy module and the processing unit respectively; the processing unit is electrically connected with the network module; the network module establishes a communication connection with the server;

the server is configured to acquire target location information provided by a first user and recommend a cryogenic physical therapy device to the first user based on a relationship between the target location information and pre-recorded location information of each of the cryogenic physical therapy devices; the server is further configured to determine whether an account balance of the first user meets a fee deduction condition after the first user selects a target cryogenic physical therapy device, and send a use request to a network module corresponding to the target cryogenic physical therapy device when determining that the account balance meets the fee deduction condition, wherein the use request includes a start time, a duration and a physical therapy temperature;

the processing unit is configured to acquire the use request received by the network module, generate a control instruction based on the use request, and send the control instruction to the programmable controller;

the programmable controller is configured to control the physical therapy module to execute an operation indicated by the control instruction when receiving the control instruction; the programmable controller is further configured to send end information to the processing unit after the first user has completed cryogenic physical therapy;

the processing unit is further configured to generate a fee deduction request based on the end information and send the fee deduction request to the server through the network module; and the server is further configured to update the account balance of the first user when receiving the fee deduction request.

Optionally, each of the cryogenic physical therapy devices further includes a sensing module, which is electrically connected with the programmable controller;

the sensing module is configured to acquire sensing data of the cryogenic physical therapy device and send the sensing data to the programmable controller;

the programmable controller is configured to determine an operating state of the cryogenic physical therapy device based on the sensing data and/or the received control instruction, and send operating state information corresponding to the operating state to the processing unit, wherein the operating state includes a working state, a reserved state and a standby state;

the processing unit is configured to generate a state updating request based on the operating state information and send the state updating request to the server; and the server is configured to update pre-recorded operating state information of each of the cryogenic physical therapy devices when receiving the state updating request; the server is further configured to recommend a cryogenic physical therapy device whose operating state is the standby state to the first user.

Optionally, the physical therapy module includes a refrigeration unit, a heating unit and an air outlet unit, and the programmable controller is electrically connected with the refrigeration unit, the heating unit and the air outlet unit respectively; and the programmable controller is further configured to control the refrigeration unit to carry out a refrigerating operation, control the heating unit to carry out a heating operation and control the air outlet unit to change an air speed based on the sensing data and/or the received control instruction.

Optionally, each of the human-machine interaction devices further includes an identification module, and each of the cryogenic physical therapy devices further includes an electrically controlled cabin door; the identification module is electrically connected with the processing unit, and the electrically controlled cabin door is electrically connected with the programmable controller;

the server is configured to send authentication information of the first user to a network module corresponding to the target cryogenic physical therapy device when determining that the account balance of the first user meets the fee deduction condition;

the identification module is configured to acquire target feature information of a target user; the processing unit is configured to acquire the authentication information received by the network module, generate a cabin door opening signal when determining that the target feature information matches the authentication information, and send the cabin door opening signal to the programmable controller; and the programmable controller is configured to control the electrically controlled cabin door to be opened when receiving the cabin door opening signal.

Optionally, the server establishes a communication connection with a first user device; and the server is configured to acquire first feature information and/or recharge information input by a second user through the first user device, and update authentication information of the second user based on the first feature information, and update account balance of the second user based on the recharge information.

Optionally, each of the human-machine interaction devices further includes a playing module, which is electrically connected with the processing unit;

the server is configured to acquire audio and video resources input by the second user through the first user device and send the audio and video resources to the processing unit; and the processing unit is configured to acquire the audio and video resources and control the playing module to play the audio and video resources during cryogenic physical therapy of the second user.

Optionally, each of the human-machine interaction devices further includes a positioning module, which is electrically connected with the processing unit;

the positioning module is configured to acquire positioning information of a corresponding cryogenic physical therapy device and send the positioning information to the processing unit;

the processing unit is configured to send the positioning information to the server; and the server is configured to update the pre-recorded location information of each of the cryogenic physical therapy devices based on the positioning information.

Optionally, the server establishes a communication connection with a second user device;

the server is configured to acquire operating information input by a merchant of each of the cryogenic physical therapy devices through the second user device and record the operating information corresponding to this cryogenic physical therapy device; wherein, the operating information comprises business hours and prices for physical therapy of the cryogenic physical therapy device; and the server is further configured to display, when recommending a cryogenic physical therapy device to the first user, operating information corresponding to the recommended cryogenic physical therapy device.

Optionally, the server establishes a communication connection with a third user device;

the programmable controller is further configured to determine whether an abnormal situation occurs in a cryogenic physical device based on a device state of the cryogenic physical therapy device, and send abnormal information to the processing unit if the abnormal situation occurs in the cryogenic physical device;

the processing unit is configured to generate a prompt message based on the abnormal information and send the prompt message to the server through the network module; and the server is configured to generate a maintenance request based on the prompt message and send the maintenance request to the third user device.

Optionally, the server includes a database and an arithmetic unit;

the database is configured to record at least one of the following information: location information of each of the cryogenic physical therapy devices, operating state information of each of the cryogenic physical therapy devices, an account balance of each of users, authentication information of each of users and operating information of each of the cryogenic physical therapy devices;

the arithmetic unit is configured to update the location information of each of the cryogenic physical therapy devices based on positioning information of a cryogenic physical therapy device acquired by the positioning module; the arithmetic unit is further configured to update the operating state information of each of the cryogenic physical therapy devices based on the state updating request sent by the processing unit;

the arithmetic unit is further configured to update the account balance of the user based on the fee deduction request sent by the processing unit and/or recharge information input by the user through the first user device; the arithmetic unit is further configured to update the authentication information of the user based on first feature information input by the user through the first user device;

the arithmetic unit is further configured to update operating information of a cryogenic physical therapy device based on the operating information input by a merchant of this corresponding cryogenic physical therapy device through the second user device; and the arithmetic unit is further configured to perform income distribution between a merchant of the target cryogenic physical therapy device and a device manufacturer of the target cryogenic physical therapy device according to a preset ratio when updating the account balance of the user.

The embodiments of the invention have the following beneficial effects:

the cryogenic physical therapy system provided by the embodiments of the invention includes cryogenic physical therapy devices, human-machine interaction devices and a server, wherein each of the cryogenic physical therapy devices includes a physical therapy module and a programmable controller, and each of the human-machine interaction device includes a processing unit and a network module; wherein, the programmable controller is electrically connected with the physical therapy module and the processing unit respectively; the processing unit is electrically connected with the network module; the network module establishes a communication connection with the server. The server is configured to acquire the target location information provided by a first user, and recommend a cryogenic physical therapy device to the first user based on the relationship between the target location information and the pre-recorded location information of each of the cryogenic physical therapy devices; the server is further configured to determine whether an account balance of the first user meets the fee deduction condition after the first user selects a target cryogenic physical therapy device, and send a use request to a network module corresponding to the target cryogenic physical therapy device when determining that the account balance meets the fee deduction condition, wherein the use request includes a start time, a duration and a physical therapy temperature. The processing unit is configured to acquire the use request received by the network module, generate a control instruction based on the use request, and send the control instruction to the programmable controller. The programmable controller is configured to control the physical therapy module to execute an operation indicated by the control instruction when receiving the control instruction; the programmable controller is also configured to send end information to the processing unit after the first user has completed cryogenic physical therapy. The processing unit is further configured to generate a fee deduction request based on the end information and send the fee deduction request to the server through the network module. The server is further configured to update the account balance of the first user when receiving the fee deduction request. It can be seen that since the location information of each of the cryogenic physical therapy devices is pre-recorded, the server can recommend, after acquiring the target location information provided by the user, a cryogenic physical therapy device closer to the target location information to the user, and the server can update account information of the user after the user has completed cryogenic physical therapy. Therefore, the user does not need to go to a specific service merchant, and can select a suitable cryogenic physical therapy device according to actual conditions to perform cryogenic physical therapy. Of course, it is not necessary to achieve all the advantages mentioned above at the same time to implement any product or method of the invention.

BRIEF DESCRIPTION OF THE DRAWINGS

In order to more clearly describe the technical solutions of the embodiments of the invention and the prior art, accompanying drawings that need to be used in the embodiments and the prior art will be briefly described below. Obviously, accompanying drawings described below are for only some of embodiments of the invention. Those skilled in the art may also obtain other embodiments based on these accompanying drawings.

DETAILED DESCRIPTION

In the following, the technical solutions in the embodiments of the invention will be clearly and completely described with reference to the accompanying drawings. Obviously, the described embodiments are only some, and not all, of the embodiments of the invention. All other embodiments obtained based on the embodiments of the invention by those skilled in the art fall into the scope of protection of the invention.

In order to allow a user to select a suitable cryogenic physical therapy device according to actual situations to perform cryogenic physical therapy quickly, an embodiment of the invention provides an intelligent shared cryogenic physical therapy system. In the following, the intelligent shared cryogenic physical therapy system provided by the embodiment of the invention is described.

Figure 1:
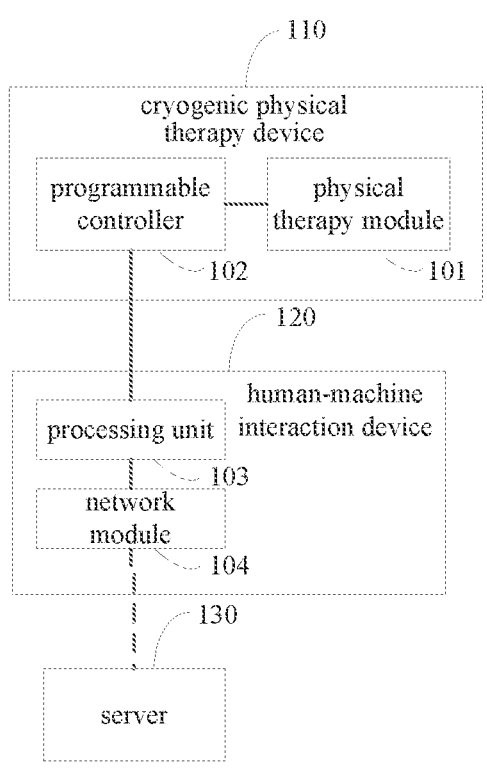
FIG. 1 is a schematic structure diagram of an intelligent shared cryogenic physical therapy system provided by an embodiment of the invention.

As shown in FIG. 1, the intelligent shared cryogenic physical therapy system includes a cryogenic physical therapy device 110, a human-machine interaction device 120 and a server 130, wherein the cryogenic physical therapy device 110 includes a physical therapy module 101 and a programmable controller 102; the human-machine interaction device 120 includes a processing unit 103 and a network module 104, wherein:

the programmable controller 102 is electrically connected with the physical therapy module 101 and the processing unit 103 respectively; the processing unit 103 is electrically connected with the network module 104; the network module 104 establishes a communication connection with the server 130.

the server 130 is configured to acquire target location information provided by a first user, and recommend a cryogenic physical therapy device to the first user based on a relationship between the target location information and pre-recorded location information of each of cryogenic physical therapy devices; the server 130 is further configured to determine whether an account balance of the first user meets a fee deduction condition after the first user selects a target cryogenic physical therapy device, and send a use request to a network module 104 corresponding to the target cryogenic physical therapy device when determining that the account balance meets the fee deduction condition, wherein the use request includes a start time, a duration time and a physical therapy temperature.

The processing unit 103 is configured to acquire the use request received by the network module 104, generate a control instruction based on the use request, and send the control instruction to the programmable controller 102.

The programmable controller 102 is configured to control the physical therapy module 101 to execute an operation indicated by the control instruction when receiving the control instruction; the programmable controller 102 is also configured to send end information to the processing unit 103 after the first user has completed cryogenic physical therapy.

The processing unit 103 is further configured to generate a fee deduction request based on the end information and send the fee deduction request to the server 103 through the network module 104.

The server 130 is also configured to update the account balance of the first user when receiving the fee deduction request.

It can be seen that the cryogenic physical therapy system provided by the embodiment of the invention includes the cryogenic physical therapy device, the human-machine interaction device and the server, wherein the cryogenic physical therapy device includes the physical therapy module and the programmable controller, and the human-machine interaction device includes the processing unit and the network module; wherein, the programmable controller is electrically connected with the physical therapy module and the processing unit respectively; the processing unit is electrically connected with the network module; the network module establishes a communication connection with the server. The server is configured to acquire the target location information provided by the first user, and recommend a cryogenic physical therapy device to the first user based on the relationship between the target location information and the pre-recorded location information of each of cryogenic physical therapy devices; the server is further configured to determine whether the account balance of the first user meets the fee deduction condition after the first user selects a target cryogenic physical therapy device, and send a use request to the network module corresponding to the target cryogenic physical therapy device when determining that the account balance meets the fee deduction condition, wherein the use request includes a start time, a duration and a physical therapy temperature. The processing unit is configured to acquire the use request received by the network module, generate a control instruction based on the use request, and send the control instruction to the programmable controller. The programmable controller is configured to control the physical therapy module to execute an operation indicated by the control instruction when receiving the control instruction; the programmable controller is also configured to send end information to the processing unit after the first user has completed cryogenic physical therapy. The processing unit is further configured to generate a fee deduction request based on the end information and send the fee deduction request to the server through the network module. The server is further configured to update the account balance of the first user when receiving the fee deduction request. It can be seen that since the location information of each of the cryogenic physical therapy devices is recorded in advance, the server can recommend, after acquiring the target location information provided by the user, a cryogenic physical therapy device closer to the target location information to the user, and the server can update account information of the user after the user has completed cryogenic physical therapy. Therefore, the user does not need to go to a specific service merchant and can select a suitable cryogenic physical therapy device according to actual situations to perform cryogenic physical therapy quickly.

The above intelligent shared cryogenic physical therapy system may include the cryogenic physical therapy device 110, the human-machine interaction device 120 and the server 130. The cryogenic physical therapy device 110 may include the physical therapy module 101 and the programmable controller 102. The cryogenic physical therapy device 110 may be various types of device providing cryogenic physical therapy services to users, including a cryogenic physical therapy cabin and a cryogenic physical therapy room, which is not specifically limited here. The physical therapy module 101 can reduce an internal temperature of the cryogenic physical therapy device to provide an extremely low temperature environment required for cryogenic physical therapy. The programmable controller 102 is a control apparatus of the cryogenic physical therapy device, which can be pre-programmed before the cryogenic physical therapy device leaves the factory such that the programmable controller 102 executes instructions of storage, logical operation, sequence control, timing, counting and arithmetic operation and other operations, and controls other components connected with it in the cryogenic physical therapy device through an input and output interface. In technical solutions provided by the embodiment of the invention, the programmable controller 102 can control the physical therapy module 101 to perform the operation indicated by the received control instruction based on the received control instruction.

The human-machine interaction device 120 can include a processing unit 103 and a network module 104. The processing unit 103 communicates with the server 130 through the network module 104 and is connected with the programmable controller 102, so that the human-machine interaction device 120 can control information interaction between the server 130 and the cryogenic physical therapy device 110. Specifically, the processing unit 103 can be an electronic device such as a computer, an embedded single chip microcomputer, an intelligent controller, etc., which is not specifically limited here. The communication connection mode between the network module 104 and the server 130 can be 4G network connection, 5G network connection, WIFI (Wireless Fidelity) connection, etc., which is not specifically limited here.

The processing unit 103 can generate, based on the use request sent by the server 130, the control instruction that can be read and executed by the programmable controller 102, so that the programmable controller 102 can control the physical therapy module 101 to perform the operation indicated by the control instruction when receiving the control instruction. The processing unit 103 can also generate the fee deduction request based on the end information sent by the programmable controller 102, and send the fee deduction request to the server 130 through the network module 104, so that the server 130 can perform the corresponding fee deduction operation.

The server 130 can provide a large amount of data storage space and various types of processing services. The server 130 can be a cloud server. In one embodiment, the processing services provided by the server 130 can include financial management, device maintenance, reservation operation, member information, recharge payment, location inquiry, etc.

In the technical solution provided by the embodiment of the invention, when a first user wants to perform the cryogenic physical therapy, the first user can provide the target location information to the server 130, and the target location information can be represented as the target location for the first user to perform the cryogenic physical therapy. For example, when the first user rests at home on weekends, the provided target location information can be location information of a location where the first user is located, so that the first user can perform the cryogenic physical therapy at a cryogenic physical therapy device near home. In one embodiment, the first user can also provide the target location information and an appointment time for cryogenic physical therapy, so that the first user can go to a location corresponding to the target location information within the appointment time to perform the cryogenic physical therapy. For example, when the first user wants to perform the cryogenic physical therapy during a business trip, the first user can provide the target location information on the business trip and a time to arrive at the location to complete a cryogenic physical therapy appointment. Then, after the current time reaches the appointment time, the first user can go to the cryogenic physical therapy device at the target location to perform cryogenic physical therapy.

The server 130 can acquire the target location information provided by the first user, and the first user can go to a merchant of the cryogenic physical therapy device to provide the target location information. In one embodiment, the first user can also provide the target location information through an intelligent device communicatively connected with the server 130, such as an electronic device such as a mobile phone, a tablet computer, a computer, etc. The first user can conveniently select a target location to perform the cryogenic physical therapy through an application client on the intelligent device. The server 130 pre-records the location information of each of the cryogenic physical therapy devices, which can be location information provided when each cryogenic physical therapy device is installed for the first time. The location information recorded by the server can also be updated in response to the change of the installation position of the cryogenic physical therapy device.

Further, the server 130 can recommend a cryogenic physical therapy device to the first user based on the relationship between the target location information and the pre-recorded location information of each of the cryogenic physical therapy devices. The server 130 can select a cryogenic physical therapy device that is closer to the target location information provided by the first user, and can also recommend a cryogenic physical therapy device that the first user may be interested in according to history of cryogenic physical therapy of the first user, for example, it can provide cryogenic physical therapy devices with different additional services for different prices.

After the first user selects the target cryogenic physical therapy device, since the server 130 records account information of each user in advance, it can be determined whether the account balance of the first user meets the fee deduction condition. The fee deduction condition can be comprehensively considered based on conditions such as the different cryogenic physical therapy device selected by the user, the duration of cryogenic physical therapy, and whether the appointment time is during a use peak period, and so on, which is not limited here. In one embodiment, the merchant of the cryogenic physical therapy device can also provide member services, and the server 130 can record member service information of each user, which can be updated in real time during the process of cryogenic physical therapy. For example, the member service information can include information such as remaining usage times with the member validity period of the member, making it more convenient for the user to perform cryogenic physical therapy, which is not specifically limited here.

The server 130 can send the use request to a network module 104 corresponding to the target cryogenic physical therapy device when determining that the account balance of the first user meets the fee deduction condition, wherein the use request includes a start time, a duration and a physical therapy temperature. Further, the processing unit 103 can acquire the use request received by the network module 104, generate the control instruction based on the use request, and send the control instruction to the programmable controller 102.

The programmable controller 102 can receive the control instruction and control the physical therapy module 101 to perform the operation indicated by the control instruction. That is, after the current time reaches the start time corresponding to the use request, the programmable controller 102 can control the physical therapy module 101 to reduce the temperature of the cryogenic physical therapy device 110 until the temperature of the cryogenic physical therapy device 110 reaches the physical therapy temperature corresponding to the use request, and the physical therapy module 101 maintains the temperature. At this time, the first user can perform cryogenic physical therapy in the cryogenic physical therapy device 110. The programmable controller 102 can also send end information to the processing unit 103 after the first user has completed cryogenic physical therapy. That is, after a duration during which the first user performs the cryogenic physical therapy reaches the duration corresponding to the use request, the programmable controller 102 can control the physical therapy module 101 to stop maintaining the physical therapy temperature corresponding to the use request. When the first user has completed cryogenic physical therapy, the programmable controller 102 can send end information to the processing unit 103, which indicates that the first user has finished the cryogenic physical therapy and the fee can be deducted.

The processing unit 103 can generate the fee deduction request based on the end information, and send the fee deduction request to the server 130 through the network module 104. Then the server 130 can receive the fee deduction request and update the account balance of the first user, i.e., deduct the account balance of the first user, and an amount of the deduction is an amount indicated by the fee deduction condition for which the first user selects the target cryogenic physical therapy device.

It can be seen that in the above intelligent shared cryogenic physical therapy system, since the server pre-records the location information of each of the cryogenic physical therapy devices, the server can recommend, after acquiring the target location information provided by the user, a cryogenic physical therapy device closer to the target location information to the user, and the server can update the account information of the user after the user has completed cryogenic physical therapy. Therefore, the user does not need to go to a specific service merchant, and can select a suitable cryogenic physical therapy device according to actual conditions to perform cryogenic physical therapy quickly. A cryogenic physical therapy device can be provided to different users at different time periods, thereby reducing the requirements for cryogenic physical therapy and better meeting the cryogenic physical therapy needs of more and more users.

Figure 2:
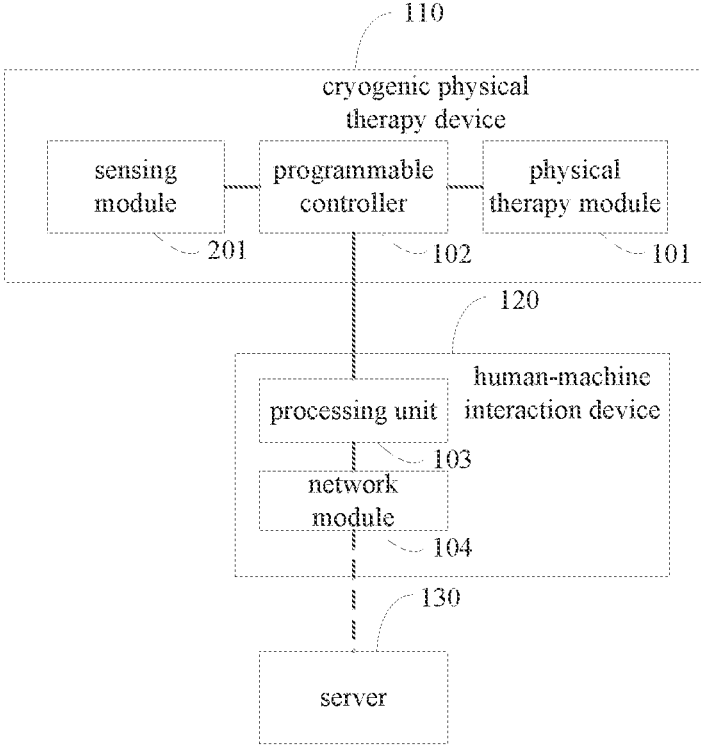
FIG. 2 is a schematic diagram of a configuration of a sensing module based on the embodiment shown in FIG. 1.

In an implementation of the embodiment of the invention, as shown in FIG. 2, the above cryogenic physical therapy device 110 can further include a sensing module 201, which is electrically connected with the programmable controller 102; the sensing module 201 is configured to acquire sensing data of the cryogenic physical therapy device 110 and send the sensing data to the programmable controller 102; the programmable controller 102 is configured to determine an operating state of the cryogenic physical therapy device 110 based on the sensing data and/or the received control instruction, and send operating state information corresponding to the operating state to the processing unit 103, wherein the operating state includes a working state, a reserved state and a standby state; the processing unit 103 is configured to generate a state updating request based on the operating state information and send the state updating request to the server 130; the server 130 is configured to update pre-recorded operating state information of each of the cryogenic physical therapy devices when receiving the state updating request; the server 130 is further configured to recommend a cryogenic physical therapy device whose operating state is the standby state to the first user.

In an implementation, the cryogenic physical therapy device 110 can also include a sensing module 201, which can include various types of sensing devices and apparatus, such as a temperature sensor, a humidity sensor, a human body sensor, a timer, a camera, etc., which is not specifically limited here. The sensing module 201 can acquire sensing data of the cryogenic physical therapy device 110, which is data of internal environment of the cryogenic physical therapy device 110 acquired by the sensing module 201, and can include data such as temperature data acquired by the temperature sensor, humidity data acquired by the humidity sensor, human body data detected by the human body sensor, monitoring video of interior of the cryogenic physical therapy device 110 acquired by the camera, cryogenic physical therapy duration obtained by the timer and the like.

The sensing module 201 can also send the acquired sensing data to the programmable controller 102, and then the programmable controller 102 can determine the operating state of the cryogenic physical therapy device 110 based on the sensing data and/or the received control instruction, wherein the operating state of the cryogenic physical therapy device 110 can include a working state, a reserved state and a standby state. For example, the sensing data acquired by the sensing module 201 includes the temperature data of −110° C. acquired by the temperature sensor and the presence of a user for physical therapy inside the cryogenic physical therapy device 110 detected by the human body sensor, and the programmable controller 102 can determine that the operating state of the cryogenic physical therapy device 110 is the working state based on the above sensing data. For another example, when the sensing data acquired by the sensing module 201 includes temperature data acquired by the temperature sensor which is −30° C., and the absence of a user for physical therapy inside the cryogenic physical therapy device 110 detected by the human body sensor, and the programmable controller 102 can determine that the current time does not reached the start time of the cryogenic physical therapy corresponding to the received control instruction, thus the programmable controller can determine the operating state of the cryogenic physical therapy device 110 is the reserved state.

Further, the programmable controller 102 can send the corresponding operating state information to the processing unit 103, and the processing unit 103 can generate a state updating request based on the operating state information and send the state updating request to the server 130. The server 130 can update the operating state information of the cryogenic physical therapy device 110 when receiving the state updating request, that is, change the pre-recorded operating state of the cryogenic physical therapy device 110 to an operating state corresponding to the state updating request, so that the server can update the operating state information of each of the cryogenic physical therapy devices.

The server can record and update the operating state information of each of the cryogenic physical therapy devices, so that the server can recommend a cryogenic physical therapy device whose operating state is the standby state to the first user when recommending a cryogenic physical therapy device to the first user, so as to reduce a waiting time of the first user.

It can be seen that, in the embodiment, the programmable controller can determine an operating state of a cryogenic physical therapy device based on the sensing data of the cryogenic physical therapy device acquired by the sensing module and/or the received control instruction, and send the operating state information corresponding to the operating state to the processing unit. The processing unit can generate a state updating request based on the operating state information and send the state updating request to the server. Further, the server can update the pre-recorded operating state information of each of the cryogenic physical therapy devices when receiving the state updating request. Further, the server can recommend a cryogenic physical therapy device whose operating state is the standby state to the first user, so as to reduce the waiting time of the first user and improve use experience of the first user.

Figure 3:
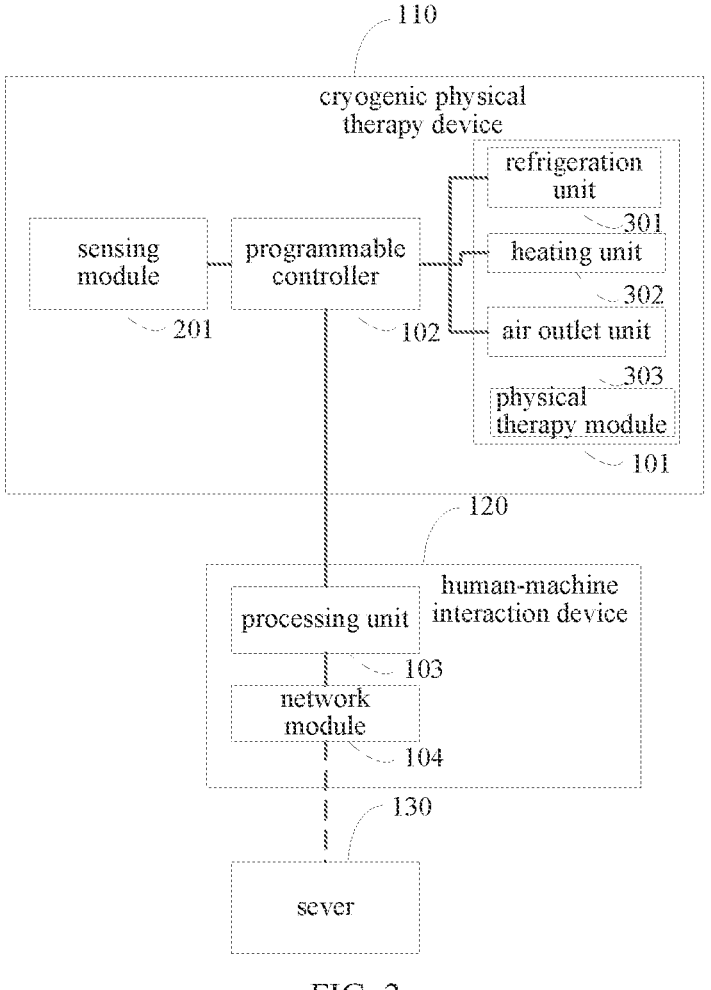
FIG. 3 is a schematic diagram of a specific structure of a physical therapy module based on the embodiment shown in FIG. 2.

In an implementation of the embodiment of the invention, as shown in FIG. 3, the above physical therapy module 101 can include a refrigeration unit 301, a heating unit 302 and an air outlet unit 303, and the programmable controller 102 is electrically connected with the refrigeration unit 301, the heating unit 302 and the air outlet unit 303 respectively; the programmable controller 102 is also configured to control the refrigeration unit 301 to carry out a refrigerating operation, control the heating unit 302 to carry out a heating operation and control the air outlet unit 303 to change an air speed based on the sensing data and/or the received control instruction.

The physical therapy module 101 can include the refrigeration unit 301, the heating unit 302, and the air outlet unit 303. The refrigeration unit 301 is an apparatus for reducing an internal temperature of the cryogenic physical therapy device, and can provide the first user with an extremely low-temperature environment required for cryogenic physical therapy. The refrigeration mode of the refrigeration unit 301 may be various, for example, the refrigeration unit 301 can refrigerate by using electric energy and using a compressor for charging refrigerant, and can also refrigerate through liquid nitrogen vaporization, which is not specifically limited here, as long as the refrigeration unit 301 can provide the extremely low temperature environment required for cryogenic physical therapy. The heating unit 302 can rapidly increase the internal temperature of the cryogenic physical therapy device to reduce a risk of frostbite of the first user during the cryogenic physical therapy, and can also be used to defrost the internal of the cryogenic physical therapy device, thereby improving refrigeration efficiency.

The air outlet unit 303 is configured to control air flow inside the cryogenic physical therapy device. The faster the air flow speed is, the lower the sensible temperature of the user is. Therefore, when the temperature is slightly higher, it is not necessary to spend a lot of energy for refrigerating by the refrigeration unit, but the sensible temperature of the user can be reduced by increasing the air speed of the air outlet unit 303. The air outlet unit 303 can also control a direction of air flow, so that different parts of the user's body can feel different temperatures. Because the sensitivity of the different parts of the body of the user to low temperature is different, it can better meet the cryogenic physical therapy needs of the user.

The programmable controller 102 is electrically connected with the refrigeration unit 301, the heating unit 302 and the air outlet unit 303, so that the programmable controller 102 can control the refrigeration unit 301 to carry out a refrigerating operation, control the heating unit 302 to carry out a heating operation and control the air outlet unit 303 to change the air speed based on the sensing data and/or the received control instruction. Therefore, during the cryogenic physical therapy, the internal temperature of the cryogenic physical therapy device 110 can be controlled in real time, thus providing a better cryogenic physical therapy effect for the first user. It also allows to quickly increasing the internal temperature of the cryogenic physical therapy device 110 in case of danger so as to reduce the risk of frostbite of the first user.

It can be seen that in the embodiment, the physical therapy module can include the refrigeration unit, the heating unit and the air outlet unit, and the programmable controller can control the refrigeration unit to carry out a refrigerating operation, control the heating unit to carry out a heating operation and control the air outlet unit to change the air speed based on the sensing data and/or the received control instruction, so as to provide a better cryogenic physical therapy experience for the first user, and quickly increase the internal temperature of the cryogenic physical therapy device in case of danger, thereby greatly reducing the risk of frostbite of the first user.

Figures 4, 5:
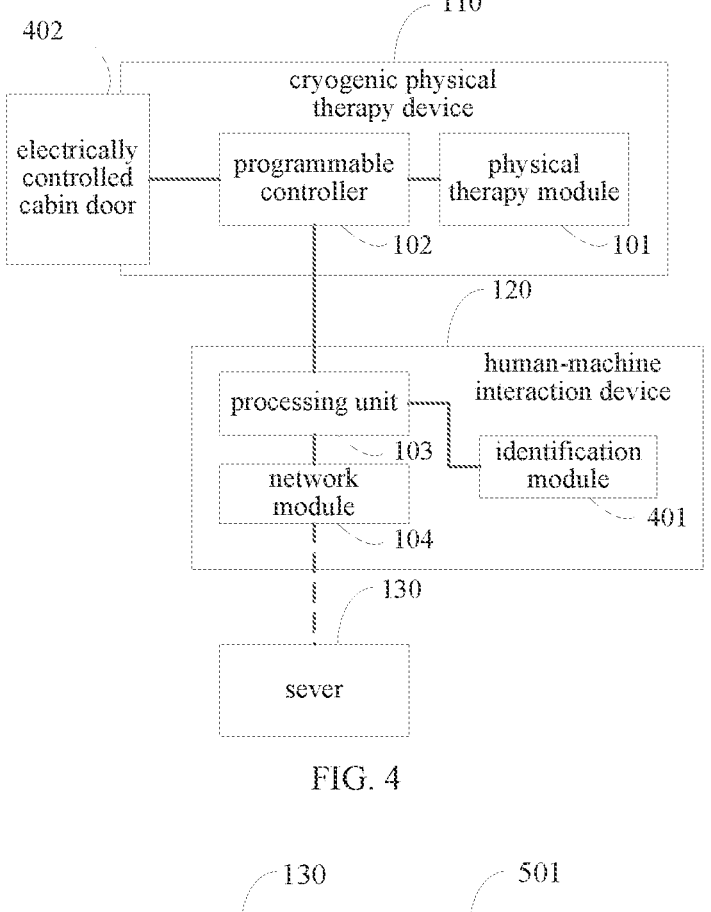
FIG. 4 is a schematic diagram of configurations of an identification module and an electrically controlled cabin door based on the embodiment shown in FIG. 1.
FIG. 5 is a schematic diagram of a configuration of a first user device based on the embodiment shown in FIG. 1.

In an implementation of the embodiment of the invention, as shown in FIG. 4, the above human-machine interaction device 120 can further include an identification module 401, and the above cryogenic physical therapy device 110 can further include an electrically controlled cabin door 402; the identification module 401 is electrically connected with the processing unit 103, and the electrically controlled cabin door 402 is electrically connected with the programmable controller 102; the server 130 is configured to send authentication information of the first user to a network module 104 corresponding to the target cryogenic physical therapy device when determining that the account balance of the first user meets the fee deduction condition; the identification module 401 is configured to acquire target feature information of a target user; the processing unit 103 is configured to acquire the authentication information received by the network module 104, generate a cabin door opening signal when determining that the target feature information matches the authentication information, and send the cabin door opening signal to the programmable controller 102; and the programmable controller is configured to control the electrically controlled cabin door 402 to be opened when receiving the cabin door opening signal.

In order to avoid use disputes caused by persons other than the first user entering the cryogenic physical therapy device, or the risk of low-temperature frostbite caused by other persons mistakenly entering the cryogenic physical therapy device, in an embodiment, the server 130 can also record the authentication information of the first user, which can be biometric information of the first user, including face feature information, fingerprint feature information, iris feature information, etc., which is not specifically limited here. In an embodiment, when the first user connects to the server 130 for the first time through a merchant of the cryogenic physical therapy device or a smart device installed with a client for the cryogenic physical therapy device, an account of the first user can be registered and information such as face feature information, fingerprint feature information and iris feature information and so on can be acquired through the merchant of cryogenic physical therapy device or the smart device. The server 130 can acquire and record the biometric information as the authentication information of the first user.

The server 130 can send the authentication information of the first user to the network module 104 corresponding to the target cryogenic physical therapy device when determining that the account balance of the first user meets the fee deduction condition. The authentication information can be the biometric information of the first user, and can also be password information provided to the first user by the server 130 in advance, information corresponding to IC (Integrated Circuit) card, information corresponding to RDFI (Radio Frequency Identification) tag, and the like.

The identification module 401 can acquire target feature information of a target user, which may be a person who wants to use the target cryogenic physical therapy device, and may include the first user. The target feature information can include biometric information of the target user, password information, information corresponding to IC card, information corresponding to RDFI tag, etc. The processing unit 103 can acquire the authentication information received by the network module 104, and compare the target feature information acquired by the identification module 401 with the authentication information received by the network module 104. When it is determined that the target feature information matches the authentication information, the processing unit 103 can generate a cabin door opening signal and send the cabin door opening signal to the programmable controller 102.

The programmable controller 102 is electrically connected with the electrically controlled cabin door 402, so the programmable controller 102 can control the electronically controlled cabin door 402 to be opened when receiving the cabin door opening signal. Therefore, the electronically controlled cabin door 402 can be opened only when the biometric information of the target user matches the authentication information, for example, when the face feature information of the target user is the same as the authentication information, or when a password input by the target user is the same as a password provided by the server 130 to the first user in advance, or when the IC card and RDFI tag carried by the target user match the authentication information. If the target feature information does not match the authentication information, the processing unit 103 will not generate a cabin door opening signal, and the electronically controlled cabin door 402 can remain closed.

It can be seen that in the embodiment, the server can send the authentication information of the first user to the network module corresponding to the target cryogenic physical therapy device; the identification module can acquire the target feature information of the target user; and the processing unit can compare the target feature information acquired by the identification module with the authentication information received by the network module and generate a cabin door opening signal when determining that the target feature information matches the authentication information, so that the programmable controller can control the electronically controlled cabin door to be opened, thereby avoid use disputes or even the risk of low-temperature frostbite caused by persons other than the first user entering the cryogenic physical therapy device.

In an implementation of the embodiment of the invention, as shown in FIG. 5, the above server 130 can establish a communication connection with a first user device 501; the server 130 is configured to acquire first feature information and/or recharge information input by a second user through the first user device 501, and update authentication information of the second user based on the first feature information, and update account balance of the second user based on the recharge information.

The server 130 can establish a communication connection with the first user device 501, wherein a manner of the communication connection may be 4G network connection, 5G network connection, WIFI (Wireless Fidelity) connection, etc., which is not specifically limited here. A user can use the first user device 501 such that the first user device 501 can exchange information with the server 130. For example, the first user device 501 can be a computer or a server installed with a remote client of the cryogenic physical therapy device, or can be a mobile phone, a tablet computer, a smart device and the like installed with software applications corresponding to the cryogenic physical therapy device, which is not specifically limited here.

Therefore, the second user can input the first feature information and/or recharge information through the first user device 510, and the first feature information can be feature information of the second user, including biometric information, preset password information, information corresponding to IC card, information corresponding to RDFI tag, etc., so that the server 130 can update the authentication information of the second user based on the first feature information. The second user can carry out cash recharging through a merchant of the cryogenic physical therapy device, or carry out online recharging or recharging member service on the account of the user through the first user device 501, and then the first user device 501 can generate recharge information. The recharge information can include account balance information of the second user or information such as member duration, available usable times and the like of the second user depending on different operations performed by the second user through the first user device 501, so that the server 130 can update the account balance of the second user based on the recharge information.

It can be seen that in the embodiment, the server can acquire the first feature information input by the second user through the first user device and update the authentication information of the second user based on the first feature information; and the server can acquire the recharge information input by the second user through the first user device and update the account balance of the second user based on the recharge information. Therefore, the user does not need to go to a merchant of the cryogenic physical therapy device to update the authentication information and recharge or the like, and the user can conveniently and quickly update the authentication information and recharge or the like through the first user device having a network connection with the server.

Figures 6, 7:
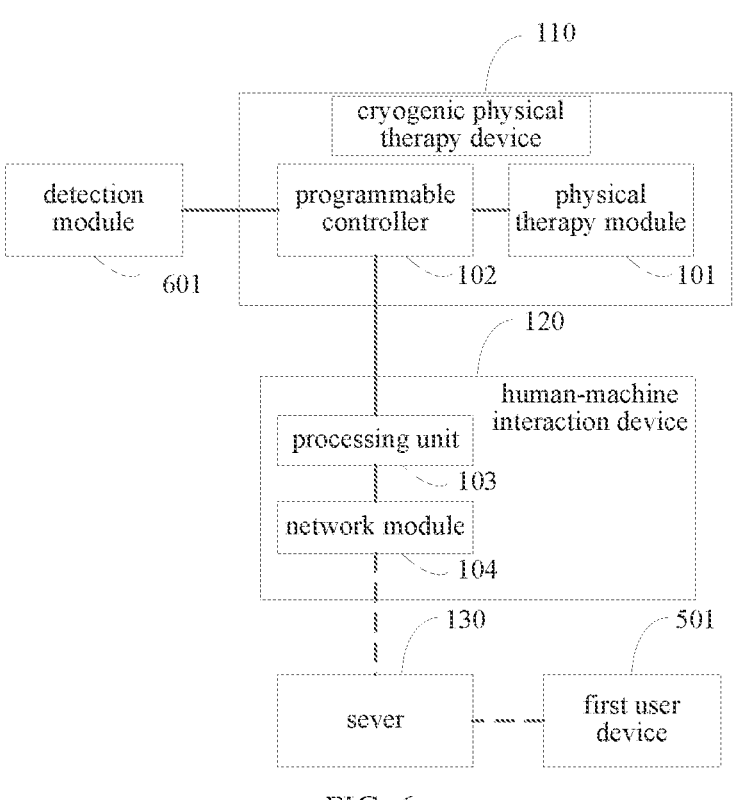
FIG. 6 is a schematic diagram of a configuration of a detection module based on the embodiment shown in FIG. 5.
FIG. 7 is a schematic diagram of a configuration of a playing module based on the embodiment shown in FIG. 5.

In an implementation of the embodiment of the invention, as shown in FIG. 6, the above cryogenic physical therapy device 110 can further include a detection module 601, which is electrically connected with the programmable controller 102; the detection module 601 is configured to detect body data of the second user and estimate energy consumption during the cryogenic physical therapy, and send the corresponding body data information and energy consumption information to the server 130; the server 130 is configured to receive the body data information and the energy consumption information, and record the body data information and the energy consumption information; the first user device 501 is configured to acquire the body data information and the energy consumption information recorded by the server 130, and display the body data information and the energy consumption information to the second user.

In an implementation, the cryogenic physical therapy device 110 can further include a detection module 601, which may be arranged outside the cryogenic physical therapy device 110. The detection module 601 can be electrically connected with the programmable controller 102, and can be configured to detect the body data of the second user and estimate the energy consumption during the cryotherapy. The cryotherapy has the function of accelerating blood circulation and burning fat continuously. Therefore, after the cryogenic physical therapy, the body data of the second user can be acquired through the detection module 601. The detection module can include devices such as a weight meter for detecting weight of the user, a body fat meter for detecting body fat of the user, a blood glucose meter for detecting blood sugar of the user, a sphygmomanometer for detecting blood pressure of the user and a heart rate meter for detecting heart rate of the user, which is not specifically limited here. The longer the duration of physical therapy and the lower the temperature of physical therapy is, the more energy the user consumes during the cryogenic physical therapy, so the detection module 601 can also estimate the energy consumption during the cryogenic physical therapy based on parameters such as the duration of physical therapy and the temperature of physical therapy of the second user and the like. Therefore, after the second user performs cryogenic physical therapy every time, the detection module 601 can acquire the body data and the energy consumption during the cryogenic physical therapy of the second user, so that the second user can intuitively understand physical changes brought about by each cryogenic physical therapy.

The detection module 601 can also send the body data information and energy consumption information corresponding to each cryogenic physical therapy of the second user to the server 130, and the server 130 can be configured to receive the body data information and energy consumption information and record the body data information and energy consumption information. Therefore, the first user device 501 can acquire the body data information and energy consumption information recorded by the server 130, and display the body data information and energy consumption information to the second user. In one implementation, the second user can set a physical therapy cycle for cryogenic physical therapy, and then in each physical therapy cycle, the second user can know changes of physical parameters in this cycle, so that the second user can set environmental parameters during cryogenic physical therapy more reasonably, and adjust a frequency for cryogenic physical therapy.

It can be seen that in the embodiment, the cryogenic physical therapy device can also include a detection module, which can be configured to detect the body data of the second user and estimate the energy consumption during the cryogenic physical therapy, so that the server can record the body data information and energy consumption information of the second user. Therefore, the first user device can intuitively display the physical changes brought about by each cryogenic physical therapy to the second user, thus greatly increasing the user's enthusiasm for cryogenic physical therapy.

In an implementation of the embodiment of the invention, as shown in FIG. 7, the above human-machine interaction device 120 can further include a playing module 701, which is electrically connected with the processing unit 103; the server 103 is configured to acquire audio and video resources input by the second user through the first user device 501 and send the audio and video resources to the processing unit 103; the processing unit 103 is configured to acquire the audio and video resources and control the playing module 701 to play the audio and video resources during cryogenic physical therapy of the second user.

When a user is performing a conventional cryogenic physical therapy, it is usually difficult to do other recreational activities in the cryogenic physical therapy device, and the process of cryogenic physical therapy is boring, and users' interest in using it will gradually decrease. In order to improve the fun during cryogenic physical therapy of the user, the human-machine interaction device 120 can further include the playing module 701, which can be electrically connected with the processing unit 103, and the playing module 701 can include electronic devices such as audio and display screen. Therefore, the second user can input audio and video resources to the server 130 through the first user device 501 during making an appointment for cryogenic physical therapy. The audio and video resources can also be built-in resources of the server 130, and the second user can select setting parameters during the cryogenic physical therapy through the server 130, such as corresponding resources, lighting effects and others.

The server 130 can acquire the audio and video resources input by the second user through the first user device 501, and send the audio and video resources to the processing unit 103. The processing unit 103 can acquire the audio and video resources through the network module 104, and further, the processing unit 103 can control the playing module 701 to play the audio and video resources during cryogenic physical therapy of the second user.

It can be seen that in the embodiment, the human-machine interaction device can also include a playing module, which can be electrically connected with the processing unit, so that the processing unit can control the playing module to play the audio and video resources pre-selected by the second user during cryogenic physical therapy of the second user, so as to enhance the fun of the process of cryogenic physical therapy and enhance the user's experience of cryogenic physical therapy.

Figure 8:
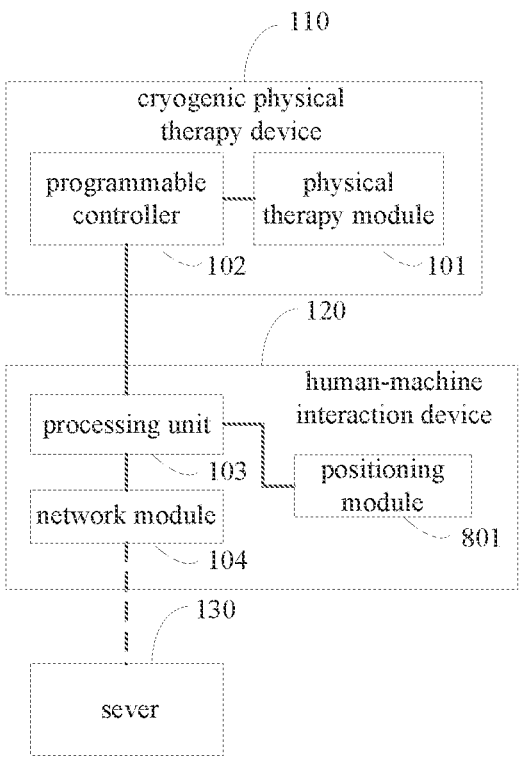
FIG. 8 is a schematic diagram of a configuration of a positioning module based on the embodiment shown in FIG. 1.

In an implementation of the embodiment of the invention, as shown in FIG. 8, the human-machine interaction device 120 can further include a positioning module 801, which is electrically connected with the processing unit 103; the positioning module 801 is configured to acquire positioning information of the cryogenic physical therapy device 110 and send the positioning information to the processing unit 103; the processing unit 103 is configured to send the positioning information to the server 130; and the server 130 is configured to update the pre-recorded location information of each of the cryogenic physical therapy devices based on the positioning information.

In an implementation, the location of a cryogenic physical therapy device can be changed. For example, the cryogenic physical therapy device can be a movable cryogenic physical therapy device, which can be movably disposed in a certain range according to use needs of the user, such as being disposed at a location closer to various large office places on weekdays, so as to meet the needs of workers for cryogenic physical therapy during work. The movable cryogenic physical therapy device can also be disposed in public places with dense traffic such as shopping malls and amusement parks and the like, to meet the cryogenic physical therapy needs of more mobile users.

Because the location of a cryogenic physical therapy device may be changed, the location information of each of the cryogenic physical therapy devices pre-recorded by the server 130 may be inaccurate, and it is difficult for a user to determine a cryogenic physical therapy device that meets the needs of the user. Therefore, the human-machine interaction device 120 can further include a positioning module 801, which may be electrically connected with the processing unit 103. Further, the positioning module 801 can acquire the positioning information of the cryogenic physical therapy device 110 and send the positioning information to the processing unit 103, the processing unit 103 can send the positioning information to the server 130. Furthermore, the server 130 can update the pre-recorded location information of each of the cryogenic physical therapy devices based on the positioning information, and the location information of each of the cryogenic physical therapy devices will be more accurate.

It can be seen that in the embodiment, the human-machine interaction device can further include a positioning module, which is electrically connected with the processing unit and configured to acquire the positioning information of a cryogenic physical therapy device. The server can update the pre-recorded location information of each of the cryogenic physical therapy devices based on the positioning information, and the positioning information of each of the cryogenic physical therapy devices will be more accurate. The location information of a cryogenic physical therapy device recommended by the server to a user is more accurate, which saves the time for the user to find a cryogenic physical therapy device, thus improving the use experience of the user.

Figure 9:
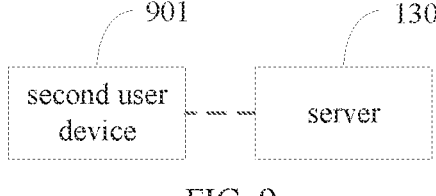
FIG. 9 is a schematic diagram of a configuration of a second user device based on the embodiment shown in FIG. 1.

In an implementation of the embodiment of the invention, as shown in FIG. 9, the above server 130 can establish a communication connection with the second user device 901; the server 130 is configured to acquire operating information input by a merchant of the cryogenic physical therapy device through the second user device 901 and record the operating information corresponding to the cryogenic physical therapy device; wherein, the operating information includes business hours and prices for physical therapy of the cryogenic physical therapy device; the server 130 is further configured to display, when recommending a cryogenic physical therapy device to the first user, operating information corresponding to the recommended cryogenic physical therapy device.

In an embodiment, the server 130 can establish a communication connection with the second user device 901, wherein a manner of the communication connection can be 4G network connection, 5G network connection, WIFI (Wireless Fidelity) connection, etc., which is not specifically limited here. The merchant of the cryogenic physical therapy device can use the second user device 901 such that the second user device 901 can exchange information with the server 130. For example, the second user device 901 can be a computer or a server installed with a remote client for the cryogenic physical therapy device, or can be a mobile phone, a tablet computer, a smart device and the like installed with software applications corresponding to the cryogenic physical therapy device, which is not specifically limited here.

The merchant of the cryogenic physical therapy device can input operating information through the second user device 901 that establishes a communication connection with the server 130, and the operating information can include the business hours and prices for physical therapy of the cryogenic physical therapy device. The merchant can set business hours according to usage time of users to meet needs of different user for cryogenic physical therapy, so that when the server 130 recommends a cryogenic physical therapy device to users, the server 130 can recommend a cryogenic physical therapy device in business. The merchant can also set the prices for physical therapy reasonably according to conditions such as different models of cryogenic physical therapy devices and the duration of cryogenic physical therapy and the like, so as to meet the cryogenic physical therapy needs of users with different consumer needs.

When recommending a cryogenic physical therapy device to the first user, the server 130 can also display the operating information corresponding to the recommended cryogenic physical therapy device, so that the first user can not only know a distance between the cryogenic physical therapy device and the target location selected by the first user, but also determine which cryogenic physical therapy devices are in business near the target location and prices for physical therapy of the cryogenic physical therapy devices, so that the first user can more conveniently select a target cryogenic physical therapy device that meets he/her own needs.

It can be seen that in the embodiment, the server can establish the communication connection with the second user device, and the merchant of the cryogenic physical therapy device can input the operating information by the second user device, so that the server can also display, when recommending a cryogenic physical therapy device to the first user, the operating information corresponding to the recommended cryogenic physical therapy device. Therefore, the first user can select a target cryogenic physical therapy device more conveniently according to the user's own needs.

Figure 10:
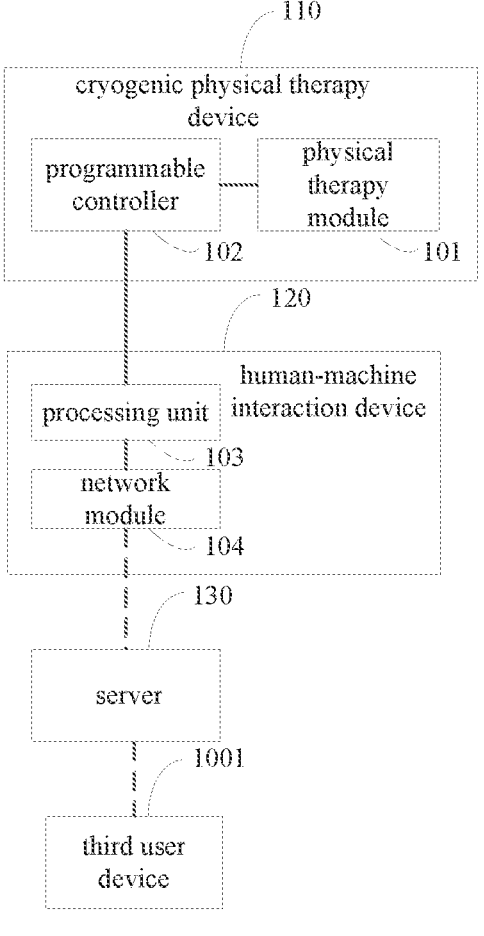
FIG. 10 is a schematic diagram of a configuration of a third user device based on the embodiment shown in FIG. 1.

In an implementation of the embodiment of the present invention, as shown in FIG. 10, the above server 130 can establish a communication connection with a third user device 1001; the programmable controller 102 is further configured to determine whether an abnormal situation occurs in the cryogenic physical therapy device 110 based on a device state of the cryogenic physical therapy device 110, and send abnormal information to the processing unit 103 if an abnormal situation occurs in the cryogenic physical therapy device; the processing unit 103 is configured to generate a prompt message based on the abnormal information and send the prompt message to the server 130 through the network module 104; and the server 130 is configured to generate a maintenance request based on the prompt message and send the maintenance request to the third user device 1001.

In an implementation, the server 130 can establish a communication connection with the third user device 1001, wherein a manner of the communication connection can be 4G network connection, 5G network connection, WIFI (Wireless Fidelity) connection, etc., which is not specifically limited here. A device manufacturer of the cryogenic physical therapy device can use the third user device 1001 such that the third user device 1001 can exchange information with the server 130. For example, the third user device 1001 can be a computer and a server and the like installed with a remote client of the cryogenic physical therapy device, which is not specifically limited here.

The programmable controller 102 can determine whether an abnormal situation occurs in the cryogenic physical therapy device 110 based on the device state of the cryogenic physical therapy device 110. The device state can include device information of the cryogenic physical therapy device 110, such as location information of the cryogenic physical therapy device 110, device usage times, device failure information and the like. In one implementation, the device state can also include the sensing data of the internal environment of the cryogenic physical therapy device acquired by the sensing module, such as temperature data, humidity data, human body data, monitoring video, duration of the physical therapy and the like, which is not specifically limited here. Further, the programmable controller 102 can determine whether an abnormal situation occurs in the cryogenic physical therapy device 110, which may include that the user has been in the cryogenic physical therapy device for too long, the electric cabin door of the cryogenic physical therapy device cannot be opened, a circuit of the cryogenic physical therapy device has failed and the like, which is not specifically limited here.

If an abnormal situation occurs in the cryogenic physical therapy device 110, the programmable controller 102 can send the abnormal information to the processing unit 103. The processing unit 103 may generate a prompt message based on the abnormal information and send the prompt message to the server 130 through the network module 104. The server 130 may generate the maintenance request based on the prompt message and send the maintenance request to the third user device 1001. Furthermore, the device manufacturer of the cryogenic physical therapy device can quickly arrange staff for personnel rescue and device maintenance based on the location information of the cryogenic physical therapy device included in the maintenance request. For example, when the abnormal situation is that the user has been in the cryogenic physical therapy device for too long, the device manufacturer of the cryogenic physical therapy device can remotely and forcibly close the cryogenic physical therapy device based on the maintenance request.

It can be seen that, in the embodiment, the server can establish a communication connection with the third user device of the device manufacturer of the cryogenic physical therapy device, so that when the programmable controller detects that an abnormal situation occurs in the cryogenic physical therapy device, the server can send the maintenance request to the third user device. Therefore, the device manufacturer of the cryogenic physical therapy device can quickly arrange staff for personnel rescue and device maintenance based on the maintenance request, so as to ensure the health of users and property safety of merchants.

Figure 11:
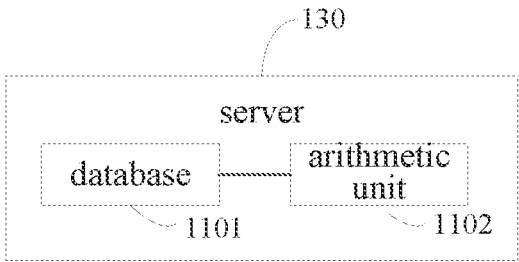
FIG. 11 is a schematic diagram of a specific structure of a database based on the embodiment shown in FIG. 1.

In an implementation of the embodiment of the invention, as shown in FIG. 11, the above server 130 can include a database 1101 and an arithmetic unit 1102; the database 1101 is configured to record at least one of the following information: location information of each of the cryogenic physical therapy devices, operating state information of each of the cryogenic physical therapy devices, an account balance of a user, authentication information of a user, body data information of the user, energy consumption information of a user and operating information of a cryogenic physical therapy device; the arithmetic unit 1102 is configured to update the location information of each of the cryogenic physical therapy devices based on positioning information of the cryogenic physical therapy device acquired by the positioning module; the arithmetic unit 1102 is further configured to update the operating state information of each of the cryogenic physical therapy devices based on a state updating request sent by the processing unit; the arithmetic unit 1102 is further configured to update the account balance of the user based on the fee deduction request sent by the processing unit and/or recharge information input by the user through the first user device; the arithmetic unit 1102 is further configured to update the authentication information of the user based on first feature information input by the user through the first user device; the arithmetic unit 1102 is further configured to update the body data information of the user based on the body data of the user detected by the detection module 601; the arithmetic unit 1102 is further configured to update the energy consumption information of the user based on the energy consumption of the user during cryogenic physical therapy detected by the detection module; the arithmetic unit 1102 is further configured to update the operating information of a corresponding cryogenic physical therapy device based on the operating information input by a merchant of this corresponding cryogenic physical therapy device through the second user device; and the arithmetic unit 1102 is also configured to perform income distribution between a merchant of the target cryogenic physical therapy device and a device manufacturer of the target cryogenic physical therapy device according to a preset ratio when updating the account balance of the user.

The server 130 can include the database 1101 and the arithmetic unit 1102. The database 1101 can record the location information of each of the cryogenic physical therapy devices to recommend a cryogenic physical therapy device closer to the target location information to the user. The database can also record the operating state information of each of the cryogenic physical therapy devices and the operating information of each of the cryogenic physical therapy devices, so as to make a more accurate recommendation to the user according to needs of the user and reduce the waiting time of the user. The database can also record the account balance of the user to determine whether the account balance of the user can meet the fee deduction condition for cryogenic physical therapy. The database can also record the authentication information of the user to avoid disputes or personal safety accidents caused by persons other than the user entering the cryogenic physical therapy device. The database can also record the body data information of the user and the energy consumption information of the user, so that the user can intuitively understand actual effects of each cryogenic physical therapy.

The arithmetic unit 1102 can update the location information of each of the cryogenic physical therapy devices and the operating state information of each of the cryogenic physical therapy devices recorded in the database 1101. The arithmetic unit can also update the account balance and authentication information of the user recorded in the database 1101. The arithmetic unit can also update the body data information and energy consumption information of the user recorded in the database 1101. The arithmetic unit can also update the operating information of the corresponding cryogenic physical therapy device recorded in the database 1101.

When updating the account balance of the user, the arithmetic unit 1102 can perform income distribution between a merchant of the target cryogenic physical therapy device and a device manufacturer of the target cryogenic physical therapy device according to the preset ratio. Because of a high price of the cryogenic physical therapy device and a high cost of one-time investment by the merchant, it is difficult to popularize the cryogenic physical therapy device. The merchant of the cryogenic physical therapy device can operate the cryogenic physical therapy device at a lower investment cost by renting instead of selling it. The merchant of the cryogenic physical therapy device and the device manufacturer of the cryogenic physical therapy device can pre-set a ratio for income distribution, so that after the user has completed cryogenic physical therapy, the cryogenic physical therapy consumption of the user can be distributed between the merchant of the cryogenic physical therapy device and the device manufacturer of the cryogenic physical therapy device according to the preset ratio.

It can be seen that in the embodiment, the server includes the database and the arithmetic unit. The database can record the location information, operating state information and operating information of each of the cryogenic physical therapy devices, and can also record the account balance, authentication information, body data information of the user and the energy consumption information of the user and the like. The arithmetic unit can update the information recorded in the database, and can also perform income distribution between a merchant of the target cryogenic physical therapy device and a device manufacturer of the target cryogenic physical therapy device according to a preset ratio when updating the account balance of the user. Thereby the investment of the merchant of the cryogenic physical therapy device is reduced, facilitating the popularization of cryotherapy, and further better meeting the needs of users for cryogenic physical therapy.

Figure 12:
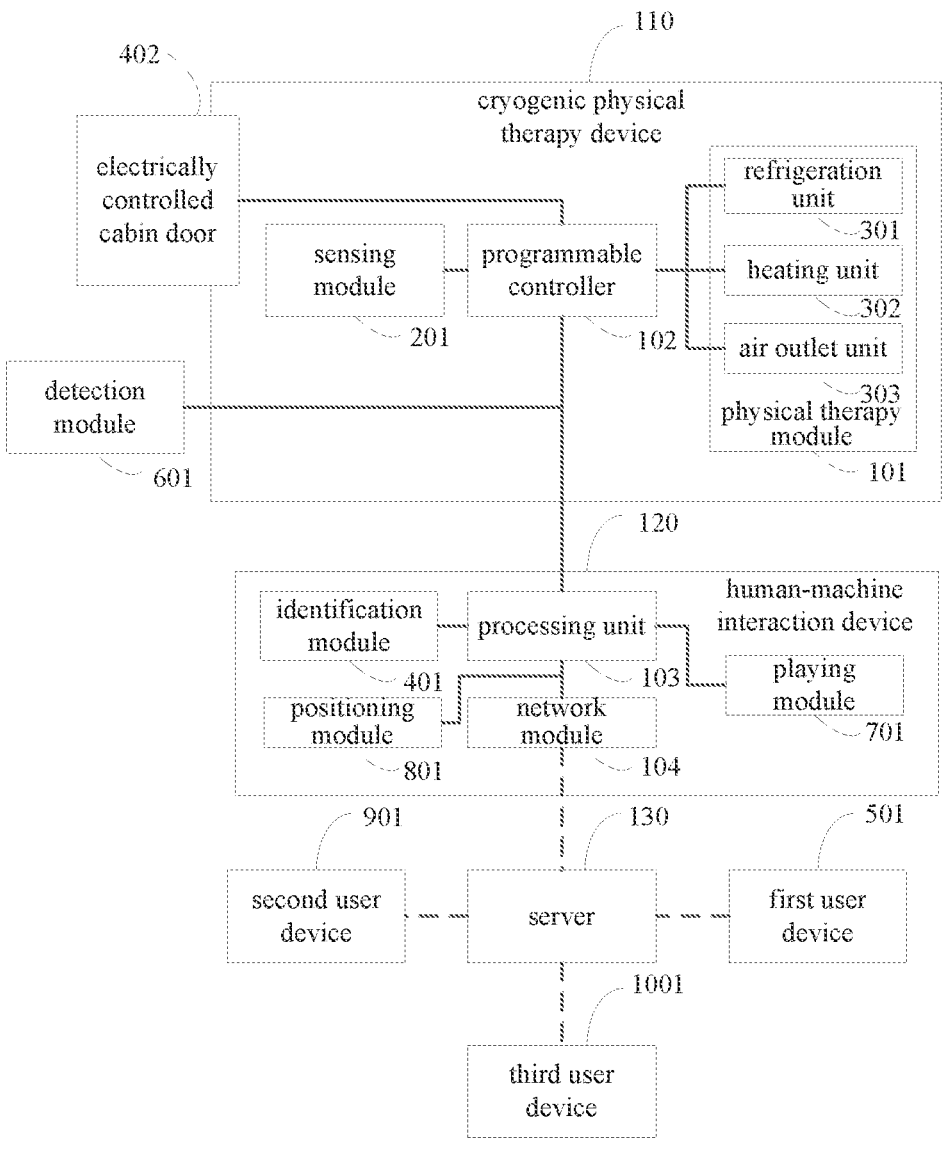
FIG. 12 is a schematic diagram of a special structure of the intelligent shared cryogenic physical therapy system based on the embodiment shown in FIG. 1.

In the following, the specific structure of the cryogenic physical therapy system is described in combination with a schematic structure diagram of an intelligent shared cryogenic physical therapy system shown in FIG. 12.

The intelligent shared cryogenic physical therapy system provided by an embodiment of the invention includes the cryogenic physical therapy device 110, the human-machine interaction device 120 and the sever 130.

The cryogenic physical therapy device 110 includes the physical therapy module 101, the programmable controller 102, the sensing module 201, the detection module 601 and the electrically controlled cabin door 402. The physical therapy module 101 includes the refrigeration unit 301, the heating unit 302, and the air outlet unit 303. The programmable controller 102 is respectively connected with the refrigeration unit 301, the heating unit 302, the air outlet unit 303, the sensing module 201, the detection module 601 and the electrically controlled cabin door 402.

The human-machine interaction device 120 includes the processing unit 103, the network module 104, the identification module 401, the playing module 701 and the positioning module 801, and the processing unit 103 is electrically connected with the network module 104, the identification module 401, the playing module 701 and the positioning module 801 respectively.

The server 130 establishes communication connections with the first user device 501, the second user device 901 and the third user device 1001, respectively. The programmable controller 102 is electrically connected with the processing unit 103, and the processing unit 103 establishes a communication connection with the server 130 through the network module 104.

It can be seen that in the intelligent shared cryogenic physical therapy system provided by the embodiment of the invention, the server can not only recommend, after acquiring the target location information provided by the user, a cryogenic physical therapy device closer to the target location information to the user, but also update the account information of the user after the user has completed cryogenic physical therapy. Therefore, the user does not need to go to a specific service merchant, and can select a suitable cryogenic physical therapy device according to actual conditions to perform cryogenic physical therapy quickly. It also allows recommending a more suitable cryogenic physical therapy device to the user based on the operating state information and operating information of each of the cryogenic physical therapy devices, which reduces the safety risk of user for cryogenic physical therapy and improves the fun during cryogenic physical therapy of the user. The investment of the merchant is also reduced, which is conducive to the promotion for cryogenic physical therapy. The Manufacturer of the cryogenic physical therapy device can quickly arrange staff for personnel rescue and device maintenance based on the maintenance request, so as to protect the health of the user and property safety of the business.

It should be noted that relational terms such as first and second and the like herein are only used to distinguish one entity or operation from another and do not necessarily require or imply any such actual relationship or order between these entities or operations. Moreover, the terms "comprising", "including" or any other variations thereof are intended to encompass a non-exclusive inclusion such that a process, method, article or device that includes a series of elements includes not only those elements, but also includes other elements not explicitly listed or other elements inherent to such a process, method, article or apparatus. Without further limitation, elements defined by the phrase "comprising one . . ." do not preclude the presence of additional identical elements in a process, method, article or device that includes the mentioned elements.

The various embodiments in this specification are described in a related manner. Each embodiment focuses on the differences from other embodiments, and the same and similar parts between the various embodiments can be referred to each other. The above descriptions are only preferred embodiments of the invention, and are not intended to limit the scope of protection of the invention. Any modifications, equivalent replacements, improvements and the like made within the spirit and principles of the disclosure shall be included within the scope of protection of the invention.

The invention claimed is:

1. An intelligent shared cryogenic physical therapy system, comprising cryogenic physical therapy devices, human-machine interaction devices and a server, wherein each of the cryogenic physical therapy devices comprises a physical therapy module and a programmable controller; each of the human-machine interaction devices comprises a processing unit and a network module; wherein:

the programmable controller is electrically connected with the physical therapy module and the processing unit respectively; the processing unit is electrically connected with the network module; the network module establishes a communication connection with the server; the server is configured to acquire target location information provided by a first user and recommend a cryogenic physical therapy device to the first user based on a relationship between the target location information and pre-recorded location information of each of the cryogenic physical therapy devices; the server is further configured to determine whether an account balance of the first user meets a fee deduction condition after the first user selects a target cryogenic physical therapy device, and send a use request to a network module corresponding to the target cryogenic physical therapy device when determining that the account balance meets the fee deduction condition, wherein the use request comprises a start time, a duration and a physical therapy temperature;

the processing unit is configured to acquire the use request received by the network module, generate a control instruction based on the use request, and send the control instruction to the programmable controller;

the programmable controller is configured to control the physical therapy module to execute an operation indicated by the control instruction when receiving the control instruction; the programmable controller is further configured to send end information to the processing unit after the first user has completed cryogenic physical therapy;

the processing unit is further configured to generate a fee deduction request based on the end information and send the fee deduction request to the server through the network module; and the server is further configured to update the account balance of the first user when receiving the fee deduction request;

wherein each of the cryogenic physical therapy device further comprises a sensing module, which is electrically connected with the programmable controller;

the sensing module is configured to acquire sensing data of the cryogenic physical therapy device and send the sensing data to the programmable controller;

the programmable controller is configured to determine an operating state of the cryogenic physical therapy device based on the sensing data and/or the received control instruction, and send operating state information corresponding to the operating state to the processing unit, wherein the operating state comprises a working state, a reserved state and a standby state;

the processing unit is configured to generate a state updating request based on the operating state information and send the state updating request to the server; and the server is configured to update pre-recorded operating state information of each of the cryogenic physical therapy devices when receiving the state updating request; the server is further configured to recommend a cryogenic physical therapy device whose operating state is the standby state to the first user;

wherein the physical therapy module comprises a refrigeration unit, a heating unit and an air outlet unit, and the programmable controller is electrically connected with the refrigeration unit, the heating unit and the air outlet unit respectively; and the programmable controller is further configured to control the refrigeration unit to carry out a refrigerating operation, control the heating unit to carry out a heating operation and control the air outlet unit to change an air speed based on the sensing data and/or the received control instruction;

the server establishes a communication connection with a third user device;

the programmable controller is further configured to determine whether an abnormal situation occurs in a cryogenic physical device based on a device state of the cryogenic physical therapy device, and send abnormal information to the processing unit if the abnormal situation occurs in the cryogenic physical device;

the processing unit is configured to generate a prompt message based on the abnormal information and send the prompt message to the server through the network module; and the server is configured to generate a maintenance request based on the prompt message and send the maintenance request to the third user device.

2. The cryogenic physical therapy system according to claim 1, wherein each of the human-machine interaction devices further comprises an identification module, and each of the cryogenic physical therapy devices further comprises an electrically controlled cabin door; the identification module is electrically connected with the processing unit, and the electrically controlled cabin door is electrically connected with the programmable controller;

the server is configured to send authentication information of the first user to a network module corresponding to the target cryogenic physical therapy device when determining that the account balance of the first user meets the fee deduction condition;

the identification module is configured to acquire target feature information of a target user; the processing unit is configured to acquire the authentication information received by the network module, generate a cabin door opening signal when determining that the target feature information matches the authentication information, and send the cabin door opening signal to the programmable controller; and the programmable controller is configured to control the electrically controlled cabin door to be opened when receiving the cabin door opening signal.

3. The cryogenic physical therapy system according to claim 1, wherein the server establishes a communication connection with a first user device; and the server is configured to acquire first feature information and/or recharge information input by a second user through the first user device, and update authentication information of the second user based on the first feature information, and update an account balance of the second user based on the recharge information.

4. The cryogenic physical therapy system according to claim 3, wherein each of the human-machine interaction devices further comprises a playing module, which is electrically connected with the processing unit;

the server is configured to acquire audio and video resources input by the second user through the first user device and send the audio and video resources to the processing unit; and the processing unit is configured to acquire the audio and video resources and control the playing module to play the audio and video resources during cryogenic physical therapy of the second user.

5. The cryogenic physical therapy system according to claim 3, wherein the server establishes a communication connection with a second user device;

the server is configured to acquire operating information input by a merchant of each of the cryogenic physical therapy devices through the second user device and record the operating information corresponding to this cryogenic physical therapy device; wherein, the operating information comprises business hours and prices for physical therapy of the cryogenic physical therapy device; and the server is further configured to display, when recommending a cryogenic physical therapy device to the first user, operating information corresponding to the recommended cryogenic physical therapy device.

6. The cryogenic physical therapy system according to claim 5, wherein the server comprises a database and an arithmetic unit;

the database is configured to record at least one of the following information: location information of each of the cryogenic physical therapy devices, operating state information of each of the cryogenic physical therapy devices, an account balance of each of users, authentication information of each of users and operating information of each of the cryogenic physical therapy devices;

the arithmetic unit is configured to update the location information of each of the cryogenic physical therapy devices based on positioning information of a cryogenic physical therapy device acquired by the positioning module; the arithmetic unit is further configured to update the operating state information of each of the cryogenic physical therapy devices based on the state updating request sent by the processing unit;

the arithmetic unit is further configured to update the account balance of the user based on the fee deduction request sent by the processing unit and/or recharge information input by the user through the first user device; the arithmetic unit is further configured to update the authentication information of the user based on first feature information input by the user through the first user device;

the arithmetic unit is further configured to update operating information of a cryogenic physical therapy device based on the operating information input by a merchant of this corresponding cryogenic physical therapy device through the second user device; and the arithmetic unit is further configured to perform income distribution between a merchant of the target cryogenic physical therapy device and a device manufacturer of the target cryogenic physical therapy device according to a preset ratio when updating the account balance of the user.

7. The cryogenic physical therapy system according to claim 1, wherein each of the human-machine interaction devices further comprises a positioning module, which is electrically connected with the processing unit;

the positioning module is configured to acquire positioning information of a corresponding cryogenic physical therapy device and send the positioning information to the processing unit;

the processing unit is configured to send the positioning information to the server; and the server is configured to update the pre-recorded location information of each of the cryogenic physical therapy devices based on the positioning information.

* * * * *